United States Patent [19]

Schickaneder et al.

[11] Patent Number: 4,659,721

[45] Date of Patent: * Apr. 21, 1987

[54] ALKANOL DERIVATIVES, AND PHARMACEUTICAL PREPARATION CONTAINING THESE COMPOUNDS

[75] Inventors: Helmut Schickaneder, Eckental; Stefan Postius, Nürnberg; Istvan Szelenyi, Schwaig; Peter Mörsdorf, Cadolzburg; Rolf Herter, Schwabach; Kurt H. Ahrens, Nürnberg, all of Fed. Rep. of Germany

[73] Assignee: Ludwig Heumann & Co. GmbH, Nürnberg, Fed. Rep. of Germany

[*] Notice: The portion of the term of this patent subsequent to Jul. 8, 2003 has been disclaimed.

[21] Appl. No.: 693,204

[22] Filed: Jan. 22, 1985

[30] Foreign Application Priority Data

Feb. 10, 1984 [DE] Fed. Rep. of Germany ....... 3404786

[51] Int. Cl.$^4$ .................... C07D 417/12; C07D 31/41

[52] U.S. Cl. .................... 514/326; 540/480; 540/603; 514/183; 546/210; 546/212; 514/212; 546/214; 546/230; 514/222; 546/232; 514/230; 548/135; 514/232; 548/214; 514/237; 548/267; 548/569; 514/255; 549/76; 549/75; 514/317; 549/77; 549/495; 514/331; 564/104; 564/306; 514/372; 564/237; 564/340; 514/471; 564/346; 514/383; 514/362; 514/438; 514/609; 514/649; 514/650; 544/152; 544/159; 544/163; 544/162; 544/165; 544/367; 544/379; 544/366; 544/398; 544/399; 544/59; 544/60; 544/111; 544/146; 546/209

[58] Field of Search .................... 544/60, 59, 111, 146, 544/152, 159, 163, 162, 165, 367, 379, 366, 398, 399; 546/209, 210, 212, 214, 230, 232; 260/239 B; 548/135, 214, 267, 569; 549/76, 75, 77, 495; 564/104, 306, 237, 340, 346; 514/183, 212, 222, 230, 232, 237, 255, 317, 326, 331, 372, 471, 383, 362, 438, 609, 649, 650

[56] References Cited

FOREIGN PATENT DOCUMENTS 2917026 11/1979 Fed. Rep. of Germany ...... 514/326
1601459 10/1981 United Kingdom ................ 514/326
2098988 12/1982 United Kingdom ................ 546/232

OTHER PUBLICATIONS

Chem. Abst. 96:79442 Algieri et al.
Chem. Abst. 96:79443k Lumma et al.

Primary Examiner—Robert T. Bond
Attorney, Agent, or Firm—Walter H. Schneider

[57] ABSTRACT

Alkanol derivatives corresponding to the general formula I

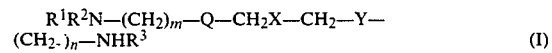

$$R^1R^2N-(CH_2)_m-Q-CH_2X-CH_2-Y-(CH_2-)_n-NHR^3 \quad (I)$$

which have a highly selective action on histamine-H$_2$ receptors are described. Due to this action, these compounds may advantageously be used for treatment of diseases caused by raised gastric secretion.

10 Claims, No Drawings

ALKANOL DERIVATIVES, AND PHARMACEUTICAL PREPARATION CONTAINING THESE COMPOUNDS

This invention relates to new alkanol derivatives which have a highly selective action on histamine-$H_2$ receptors, processes for their preparation and pharmaceutical preparations containing these compounds, and the use of these compounds in therapy.

Cimetidine and ranitidine have already been used therapeutically as anti-ulcerative agents. Both these substances, however, have a relatively short half life and are therefore required to be administered in several daily doses of tablets with dose units of 160 to 300 mg in a therapeutically determined form. There is therefore a need for anti-ulcerative agents which have a more prolonged action and/or higher activity than cimetidine or ranitidine.

Certain compounds inhibit gastric secretion due to their specific $H_2$-antagonistic activity when stimulated by histamine antagonists (Ash and Schild, "Brit. J. of Pharmacol. Chemother.", 27, 427 (1966) and Black et al., "Nature", 236, 385 (1971)). The pharmacological activity of these compounds, which is described in more detail below, may be demonstrated on the perfused rat stomach by a modified method according to DE-OS 2 734 070 or by determining the $pA_2$-values in vitro on the atrium of the guinea-pig (see Ariens, Molecular Pharmacology, Volume 1, Academic Press, New York, 1964). The $H_2$ antagonistic action can also be demonstrated on waking Heidenhain-Pouch dogs by the method of Black et al, "Nature", 236, 385 (1971) and waking fistulized cats. These compounds also antagonize the histamine action on the frequency of contraction of the isolated right atrium of the guinea-pig but have no effect on histamine induced contractions of isolated, smooth gastrointestinal muscle when these are produced by $H_2$ antagonists.

Since substances which inhibit histamine-$H_2$ receptors have an inhibitory action both on the basal gastric acid secretion and on the gastric acid secretion induced by gastrine, histamine, methacholine or food, they may be used for the treatment of peptic ulcers caused by excessive gastric acid secretion and in the treatment of hyperacidic gastritis.

It is an object of the present invention to provide new inhibitory substances for histamine-$H_2$ receptors with improved and/or more prolonged activity.

This problem is solved by the invention.

The present invention thus relates to new alkanol derivatives corresponding to the general formula I $$R^1R^2N-(CH_2)_m-Q-CH_2X-CH_2-Y-(CH_2)_n-NHR^3 \quad (I)$$

wherein $R^1$ and $R^2$, which may be identical or different, each represent hydrogen, $C_{1-10}$-alkyl, $C_{5-6}$-cycloalkyl, amino, lower alkylamino or lower dialkylamino when m=1 or $(NH_2)_2C=$ when m=0 or $R^1$ and $R^2$ together with the nitrogen atom to which they are attached represent a 5- to 8-membered, heterocyclic ring which is unsubstituted or substituted with a methyl group, m stands for 0 or 1 and Q denotes a furan, thiophene, thiazole or benzene ring, X represents a sulphur or oxygen atom or the group —CHOH, Y represents a single bond or the group —CHOH, n denotes 1 or 2 and $R^3$ represents one of the groups

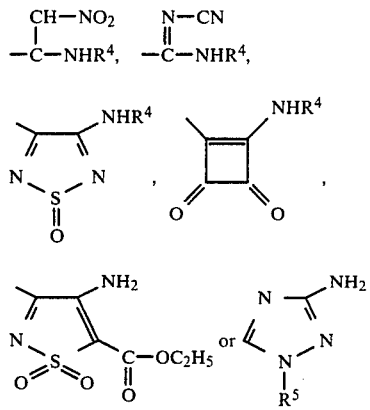

wherein $R^4$ represents a hydrogen atom, a $C_{1-3}$-alkyl group or a propargyl group, and $R^5$ represents a hydrogen atom or a $C_{1-3}$-alkyl group, and their physiologically acceptable salts and hydrates.

In the general formula I, $R^1$ and $R^2$, which may be identical or different, denote hydrogen, $C_{1-10}$-alkyl, preferably $C_{1-3}$-alkyl (lower alkyl), $C_{5-6}$-cycloalkyl such as cyclopentyl or cyclohexyl, amino or lower alkylamino such as methyl, ethyl or propylamino when m has the value 1. When m has the value 0, $R^1$ and $R^2$ together form the group $(NH_2)_2CH=$. $R^1$ and $R^2$ may also, together with the nitrogen atom to which they are attached, form a 5- to 8-membered heterocyclic ring which may be unsubstituted or substituted with a methyl group. Examples of such rings include the pyrrolidine, methylpyrrolidine, morpholine, thiomorpholine, piperidine, methylpiperidine, N-methylpiperazine, homopiperidine, heptamethyleneimino and octamethyleneimino ring, the pyrrolidine and piperidine ring being preferred.

Q denotes a furan, thiophene, thiazole or benzene ring. The furan ring is preferably inserted in the molecule in the 2,5-position. The thiophene ring is preferably inserted in the 2,5- or 2,4-position and the thiazole ring is preferably inserted in the 2,4-position. The benzene ring is preferably inserted by bonds in the 1- and 3- or 1- and 4-position. The benzene ring is preferred among these structural units, a benzene ring incorporated in the 1- and 3-position being particularly preferred.

X represents a sulphur or oxygen atom or the group —CHOH. Y denotes a single bond or the group —CHOH. The symbol n may assume the value 1 or 2. $R^3$ represents one of the following groups:

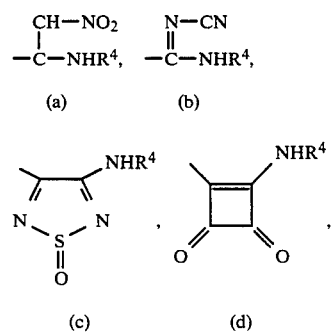

(a)      (b)

(c)      (d)

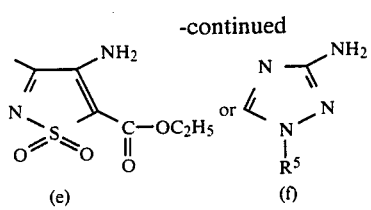

(e)  (f)

Among these units, the groups (c), (d) and (e) are preferred.

In these groups, $R^4$ represents a hydrogen atom, a $C_{1-3}$-alkyl group (lower alkyl group) or a propargyl group, and $R^5$ represents a hydrogen atom or a $C_{1-3}$-alkyl group (lower alkyl group).

When Q in the general formula I stands for a thiazole ring inserted by bonds in the 2- and 4-position, the other symbols preferably have the following meanings: $m=0$; $R^1$ and $R^2=(NH_2)_2C=$; $X=$ a sulphur atom; $Y=$ the group $-CHOH$; $n=1$, $R^3=$

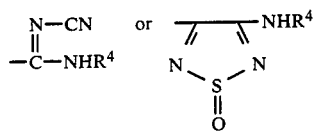

and $R^4=$ a hydrogen atom or a methyl or propargyl group.

If Q in the general formula I stands for a furan ring inserted by bonds in the 2- and 5-position or a thiophene ring inserted in the 2- and 4-position, then m preferably has the value 1 and $R^1$ is preferably a hydrogen atom. In that case, it is also preferred if $R^1$ is a $C_{1-10}$-alkyl group, in particular a $C_{1-3}$-alkyl group, and $R^2$ is a $C_{5-6}$-cycloalkyl group.

A preferred group of compounds according to the invention is characterised in that $R^1$ and $R^2$ represent methyl and/or ethyl or $R^1$ and $R^2$ together with the nitrogen atom to which they are attached represent a substituted or unsubstituted 5-membered or 6-membered alicyclic heterocyclic ring, a pyrrolidine, methylpyrrolidine, morpholine, thiomorpholine, piperidine, methylpiperidine, N-methylpiperazine, homopiperidine, heptamethyleneimino or octamethyleneimino ring, in particular a pyrrolidine or piperidine ring.

A particularly preferred group of compounds according to the invention is characterised in that $R^1$ and $R^2$ together with the nitrogen atom to which they are attached represent a substituted or unsubstituted 5- to 8-membered alicyclic heterocyclic ring is described above, in particular a pyrrolidine or piperidine ring.

Another preferred group of compounds according to the invention is characterised in that $R^1$ and $R^2$ and m have the meanings indicated above, Q represents a benzene ring which is inserted in the remainder of the molecule by attachment in the 1- and 3- or 1- and 4-position, preferably in the 1- and 3-position, X represents the group $-CHOH$, Y represents a single bond, $n=1$ or 2, and $R^3$ represents the groups indicated in claim 1 as described above.

The compounds according to the invention are prepared as follows:

(a) For the preparation of compounds in which $R^3$ represents

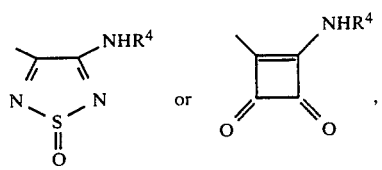

a compound corresponding to the general formula II

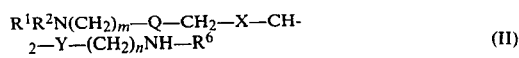

wherein $R^1$, $R^2$, m, Q, X, Y and n have the meanings indicated above and $R^6$ represents the group

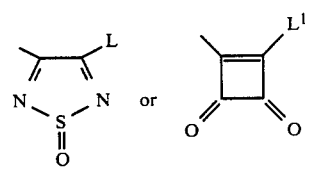

wherein $L^1$ denotes a methoxy, ethoxy or butoxy group as exit group
is reacted in a solvent with an amine corresponding to the general formula III $$R^4NH_2 \tag{III}$$

wherein $R^4$ represents a hydrogen atom, a methyl group or a propargyl group, to form the compound according to the invention corresponding to the general formula I. The reaction is carried out in a solvent, for example in an alcohol such as methanol, ethanol or isopropanol, preferably ethanol. The compound corresponding to the general formula II and the amine corresponding to the general formula III are preferably used in equimolar quantities. The reaction temperature may range from room temperature to the reflux temperature. The reaction product is worked up and isolated in the usual manner. The compound obtained is optionally converted into a physiologically acceptable salt thereof.

(b) For the preparation of compounds in which $R^3$ represents

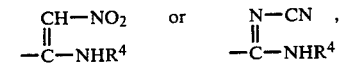

a compound corresponding to the general formula IV

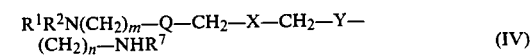

wherein $R^1$, $R^2$, m, Q, X, Y and n have the meanings indicated above and $R^7$ represents

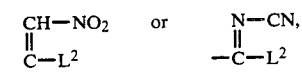

wherein $L^2$ denotes a thiomethyl, methoxy, ethoxy or phenoxy group as exit group
is reacted with an amine corresponding to the general formula III

R⁴NH₂    (III)

to form a compound according to the invention corresponding to the general formula I. The reaction is preferably carried out in a solvent such as an alcohol, e.g. methanol, ethanol or isopropanol, preferably ethanol. The reactants may, for example, be used in equimolar quantities. The reaction temperature may range from room temperature to the reflux temperature of the solvent used. The reaction product is worked up and isolated in the usual manner. The compound obtained is optionally converted into a physiologically acceptable salt thereof.

(c) For the preparation of compounds in which $R^3$ represents

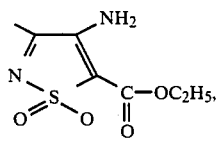

an amine corresponding to the general formula V

R¹R²N(CH₂)$_m$—Q—CH₂X—CH₂—Y—(CH₂)$_n$—NH₂    (V)

wherein $R^1$, $R^2$, m, Q, X, Y and n have the meanings indicated above
is reacted with a compound corresponding to formula VI

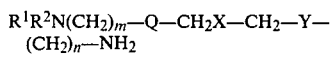

to form a compound according to the invention corresponding to the general formula I. This reaction is also preferably carried out in a solvent, for example, in an alcohol such as methanol, ethanol or isopropanol, preferably ethanol, and using equimolar quantities of reactants. The reaction temperature may range from room temperature to the reflux temperature of the solvent. The compound of formula VI used in this reaction is known and has been described, for example, in J. Org. Chem. 48, 763 (1983). The reaction product is worked up and isolated in the usual manner. The compound obtained is optionally converted into a physiologically acceptable salt thereof.

(d) For the preparation of compounds in which $R^3$ represents

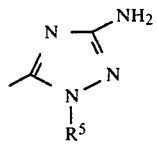

and $R^5$ represents a hydrogen atom or a methyl or ethyl group,
a compound corresponding to the general formula VII

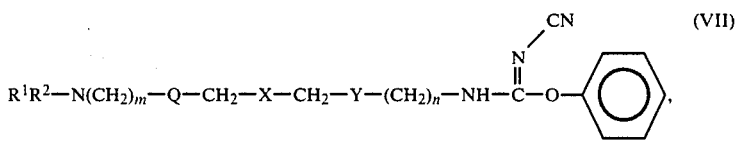

wherein $R^1$, $R^2$, m, Q, X, Y and n have the meanings indicated above, is reacted with hydrazine hydrate, methylhydrazine or ethylhydrazine in a solvent to form a compound according to the invention corresponding to the general formula I. This reaction also is preferably carried out in a solvent, for example an alcohol such as methanol, ethanol or isopropanol, preferably ethanol. The reaction may be carried out at a temperature ranging from room temperature to the reflux temperature of the solvent used and it may be carried out, for example, using equimolar quantities. The reaction product is worked up and isolated in the usual manner. The compound obtained is optionally converted into a physiologically acceptable salt thereof.

The invention also covers the various stereochemical forms (enantiomers) of the compounds of formula I and their physiologically acceptable hydrates and salts with inorganic and organic acids. These salts may be formed, for example, with mineral acids such as hydrochloric, hydrobromic or hydriodic acid, phosphoric acid, metaphosphoric acid, nitric acid or sulphuric acid or with organic acids such as formic acid, acetic acid, propionic acid, phenylacetic acid, tartaric acid, citric acid, fumaric acid, methanesulphonic acid, etc.

The compounds according to the invention may be incorporated in any desired formulations for administration. The invention therefore also covers pharmaceutical preparations containing at least one compound according to the invention for use in human or veterinary medicine. Such medicaments may be prepared by the conventional methods using one or more pharmaceutically acceptable excipients or diluents.

The compounds according to the invention may therefore be formulated for oral, buccal, local, parenteral or rectal administration, oral administration being preferred. For oral administration, the medicament may be provided, for example, in the form of tablets, capsules, powders, solutions, syrups or suspensions prepared by the conventional methods using acceptable diluents. For buccal administration, the medicaments may be provided in the form of tablets or sachets formulated in the usual manner.

The compounds according to the invention may also be made up into preparations for parenteral administration by bolus injection or continuous infusion. Formulations for injection may be prepared as ampoules of unit doses or as multiple dose containers with added preservatives.

The medicaments may assume forms such as suspensions, solutions or emulsions in oily or aqueous carriers and may contain formulating auxiliaries such as stabilizers and/or dispersing agents.

The active ingredients may also be presented in powder form to be reconstituted with a suitable carrier such as sterile, pyrogen-free water before use.

The compounds according to the invention may also be made up into preparations for rectal administration, such as suppositories or retention enemas containing, for example, the usual suppository excipients such as cocoa butter or other glycerides.

For local application, the compounds according to the invention may be incorporated in the usual formulations for ointments, creams, gels, lotions, powders or sprays.

For oral administration, a suitable daily dose of compounds according to the invention consist of 1 to 4 doses amounting to a total of 5 mg to 1 g/day, preferably 5 to 250 mg/day, depending on the patient's condition. In individual cases, it may be necessary to deviate from these quantities, depending on the individual response to the active ingredient or to the nature of its formulation and the time or interval of time at which it is administered. Thus, for example, in certain cases it will be sufficient to use less than the minimum quantity indicated above, whereas in other cases it will be necessary to exceed the maximum quantity indicated.

Compared with known medicaments recognized as highly effective for the same purposes, the compounds according to the invention are distinguished by their improved pharmacological activity. This is demonstrated by the results of the pharmaceutical comparison tests described below.

| Experimental model: Gosh-Schild rat (Stimulator: histamine) | |
|---|---|
| Cimetidine (comparison) | i.V. ID$_{50}$ 1.4 μmol/kg |
| Example 1 | i.V. ID$_{50}$ 0.075 μmol/kg |

EXAMPLE 1

(a) Preparation of
2-[2-Hydroxy-3-[3-(1-piperidylmethyl)benzyloxy]-propyl]-1H-isoindole-1,3-dione A mixture of 10.25 g (0.05 mol) of 3-(1-piperidylmethyl)-benzyl alcohol and 10.15 g (0.05 mol) of N-(2,3-epoxypropyl)-phthalimide is stirred under nitrogen for 80 minutes at 130° C. The viscous resin obtained is chromatographed on silica gel, using methylene chloride/methanol 9:1. The main fraction yields 8.60 g (42%) of the title compound in the form of a light brown oil after concentration by evaporation.

(b) Preparation of
2-Hydroxy-3-[3-(1-piperidylmethyl)-benzyloxy]-propylamine 8.60 g (0.021 mol) of 2-[2-hydroxy-3-[3-(1-piperidylmethyl)benzyloxy]propyl]-1H-isoindole-1,3-dione and 3.3 ml of hydrazine hydrate (80%) are boiled in 80 ml of ethanol for 3 hours. The residue left after concentration of the mixture by evaporation is taken up in 50 ml of water; 8 ml of conc. hydrochloric acid are added and the reaction mixture is filtered. The filtrate is adjusted to pH 12 with conc. sodium hydroxide solution and extracted with 3×40 ml methylene chloride. The organic phase is dehydrated with Na$_2$SO$_4$ and concentrated by evaporation under vacuum. The residue is distilled in a high vacuum. 4.44 g (76%) of a colourless oil, boiling point 145°–155° C./1×10$^{-2}$ mbar, are obtained.

(c) Preparation of
3-[2-Hydroxy-3-[3-(1-piperidylmethyl)benzyloxy]-propylamino]-4-ethoxy-1,2,5-thiadiazole-1-oxide A solution of 2.78 g (0.01 mol) of 2-hydroxy-3-[3-(1-piperidylmethyl)benzyloxy]propylamine in 10 ml of ethanol is added dropwise over a period of 30 minutes to a solution of 1.90 g (0.01 mol) of 3,4-diethoxy-1,2,5-thiadiazole-1-oxide in 10 ml of ethanol and the mixture is stirred at room temperature for 4 hours. The title compound obtained after concentration of the reaction solution by evaporation is reacted without further purification.

(d) Preparation of
3-[2-Hydroxy-3-[3-(1-piperidylmethyl)-benzyloxy]-propylamino]-4-amino-1,2,5-thiadiazole-1-oxide

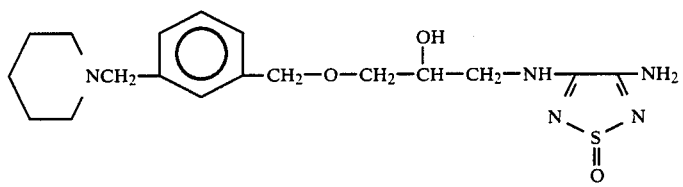

After the addition of 20 ml of ethanolic ammonia (5 mol/l) to the concentrated reaction solution mentioned above, the reaction mixture is stirred overnight. The colourless solid obtained after evaporation of the solution is chromatographed with methanol/conc. ammonia 99:1 on silica gel and yields 2.80 g (71%) of the title compound after concentration of the main fraction by evaporation. Colourless crystals, melting point 109.6°–111° C. Rf=0.49 (CH$_3$OH/NH$_3$ conc. 99:1)

C$_{18}$H$_{27}$N$_5$O$_3$S (393.5) Calculated: C 54.94; H 6.92; N 17.80; Found: C 54.87; H 6.94; N 17.78

$^1$H-NMR spectrum: (d$_6$-DMSO, TMS as internal standard): δ=1.25–1.70 (m) 6H, 2.21–2.46 (m) 4H, 3.23–3.75 (m) 4H, 3.40 (s) 2H, 3.93 (m) 1H, 4.49 (s) 2H, 5.21 (m,broad) 1H, replaceable by D$_2$O, 7.27 (s) 4H, 8.1 (m) 3H, replaceable by D$_2$O

EXAMPLE 2

(a) Preparation of
1-[2-Hydroxy-3-[3-(1-piperidylmethyl)benzyloxy]-propylamino]-2-ethoxy-cyclobutene-3,4-dione 2.78 g (0.01 mol) of 2-hydroxy-3-[3-(1-piperidylmethyl)benzyloxy]propylamine in 10 ml of ethanol are slowly added dropwise to 1.70 g (0.01 mol) of 1,2-diethoxycyclobutene-3,4-dione and the mixture is stirred for 5 hours. The title compound, which is obtained after the reaction solution has been concentrated by evaporation, is subsequently reacted without further purification.

(b) Preparation of 1-[2-Hydroxy-3-[3-(1-piperidylmethyl)benzyloxy]-propylamino]-2-amino-cyclobutene-3,4-dione

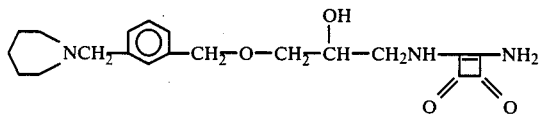

After the addition of 20 ml of ethanolic ammonia to the above mentioned reaction solution which has been concentrated by evaporation, a pale yellow precipitate is obtained. This precipitate is suction filtered after 18 hours and purified chromatographically against silica gel, using methanol.

Yield: 1.86 g (50%)

Colourless crystals, melting point 201°–203° C. (decomposition)

Rf=0.58 (CH$_3$OH/NH$_3$ conc. 99:1)

C$_{20}$H$_{27}$N$_3$O$_4$ (373.5)

$^1$H-NMR spectrum: (d$_6$-DMSO, TMS as internal standard): δ=1.28–1.62 (m) 6H, 2.19–2.42 (m) 4H, 3.25–3.93 (m) 5H, 3.40 (s) 2H, 4.48 (s) 2H, 5.22 (broad) 1H, replaceable by D$_2$O, 7.24 (s) 4H, 7.44 (broad) 3H, replaceable by D$_2$O

EXAMPLE 3

(a) Preparation of N$^1$-Cyano-N$^2$-[2-hydroxy-3-[3-(1-piperidylmethyl)benzyloxy]propyl]-S-methyl-isothiourea 1.39 g (5 mmol) of 2-hydroxy-3-[3-(1-piperidylmethyl)benzyloxy]propylamine in 25 ml of diethylether and 5 ml of methanol are slowly added dropwise to a solution of 0.73 g (5 mmol) of N-cyano-dimethyl-dithiocarbonate in 15 ml of diethylether. After 24 hours' stirring at room temperature, the solution is concentrated by evaporation under vacuum. 1.9 g of the title compound are obtained in the form of a colourless, viscous oil.

(b) Preparation of 3-Amino-5-[2-hydroxy-3-[3-(1-piperidylmethyl)benzyloxy]propylamino]-1-methyl-1H-1,2,4-triazole Yield: 0.82 g (44%)

Rf=0.55 (CH$_2$OH/conc. NH$_3$ 99:1)

C$_{19}$H$_{30}$N$_6$O$_2$ (374.5)

$^1$H-NMR spectrum: (CDCl$_3$, TMS as internal standard): δ=1.31–1.73 (m) 6H, 2.23–2.52 (m) 4H, 3.26 (s) 3H, 3.44 (s) 2H, 3.32–3.71 (m) 4H, 3.87–4.23 (m) 3H, 2H replaceable by D$_2$O, 4.50 (s) 2H, 4.77 (t, broad) 1H, replaceable by D$_2$O, ~4.8 (broad) 1H, replaceable by D$_2$O, 7.14–7.37 (s, broad) 4H.

EXAMPLE 4

(a) Preparation of 1-Chloro-3-dibenzylamino-2-propanol 4.93 g (0.25 mol) of dibenzylamine and 25.4 g (0.275 mol) of epichlorohydrin are stirred for 3 hours under nitrogen at 85° to 90° C. The golden yellow oil obtained is distilled under a high vacuum. 50.5 g (70%) of a colourless oil are obtained.

Boiling point 150°–155° C. (1.5×10$^{-2}$ mbar)

(b) Preparation of 2-Dibenzylaminomethyl-oxirane 50.7 g (0.175 mol) of 1-chloro-3-dibenzylamino-2-propanol and 9.5 g (0.24 mol) of sodium hydroxide in 5 ml of water are stirred together for one hour at 95° c. After the addition of 50 ml of chloroform and 20 ml of water, the phases are separated and the organic phase is washed with 20 ml of water, dehydrated with sodium sulphate and concentrated by evaporation. Distillation of the resulting yellow oil under vacuum yields 33.7 g (76%) of the oxirane as a colourless oil.

Boiling point 125° C. (1.5×10$^{-2}$ mbar)

(c) Preparation of 1-Dibenzylamino-3-[3-(1-piperidylmethyl)-phenyl]-2-propanol 10.2 g (0.04 mol) of 3-(1-piperidylmethyl)-bromobenzene in 20 ml of tetrahydrofuran are added dropwise to 0.97 g (0.04 mol) of magnesium filings in 5 ml of tetrahydrofuran at a reaction temperature of 60° C. This operation is followed by 30 minutes' stirring at 60° C., and the solution is then cooled to 10° C. 10.2 g (0.04 mol) of 2-benzylaminomethyl-oxirane in 20 ml of tetrahydrofurane are slowly added dropwise and the solution obtained is stirred at room temperature for 2 hours. After the addition of 20 ml of ice water and 4.5 g of ammonium chloride, the aqueous phase is separated and extracted with 25 ml of methylene chloride. The combined organic phases are dehydrated with sodium sulphate and concentrated by evaporation to yield a yellow resin which is chromatographed with methylene

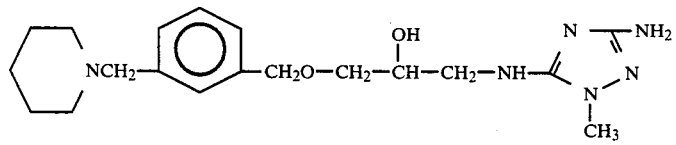

0.46 g (10 mmol) of methylhydrazine is added to a solution of 1.9 g (5 mmol) of N$^1$-cyano-N$^2$-[2-hydroxy-3-[3-(1-piperidylmethyl)benzyloxy]propyl]-S-methyl-isothiourea in 10 ml of ethanol. After 24 hours at room temperature, the solvent is evaporated off under vacuum and the residue is purified with methylene chloride/methanol 1:1 against silica gel. After evaporation of the solvent, the title compound is obtained in the form of an amorphous solid.

chloride/methanol (9:1) against silica gel. After concentration by evaporation, the second fraction yields the title compound as a pale yellow oil.

Yield: 11.5 g (67%).

(d) Preparation of 1-Amino-3-[3-(1-piperidylmethyl)phenyl]-2-propanol 11.5 g (0.027 mol) of 1-dibenzylamino-3-[3-(1-piperidylmethyl)phenyl]-2-propanol in 90 ml of ethanol and 10 ml of water are hydrogenated in the presence of 0.5 g of palladium/active charcoal (10% Pd) at 35° C. under atmospheric pressure.

After removal of the catalyst by filtration and evaporation of the solvent, 5.8 g of a colourless oil is left behind. After chromatographic purification of this oil with methanol/conc. ammonia (95:5), 3.5 g (52%) of the title compound are obtained therefrom in the form of a colourless oil.

(e) Preparation of
3-[2-Hydroxy-3-[3-(1-piperidylmethyl)phenyl]-propylamino]-4-amino-1,2,5-thiadiazole-1-oxide

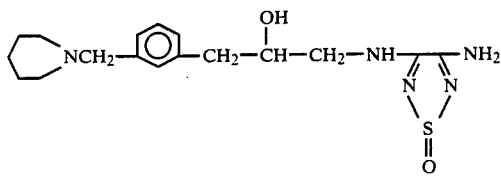

0.52 g (76%) of the title compound are obtained by a method analogous to that of Example 1 c,d from 0.47 g (1.9 mmol) of 1-amino-3-[3-(1-piperidylmethyl)phenyl]-2-propanol and 0.36 g (1.9 mmol) of 3,4-diethoxy-1,2,5-thiadiazole-1-oxide after chromatography against silica gel, using methanol/conc. ammonia (95:5) as eluent.

Colourless solid, melting point 94°–96° C.
Rf=0.55 (CH$_3$OH/NH$_3$ conc. 95:5)
C$_{17}$H$_{25}$N$_5$O$_2$S (363.5)
$^1$H-NMR spectrum: (d$_6$DMSO, TMS as internal standard): δ=1.22–1.65 (m) 6H, 2.20–2.47 (m) 4H, 2.73 (d,broad) 2H, 3.00–3.78 (m) 3H, 3.41 (s) 2H, 3.94 (m) 1H, 5.53 (broad) 1H, replaceable by D$_2$O, 7.04–7.34 (m) 4H, 8.05, 8.29 (broad) 2H, replaceable by D$_2$O

EXAMPLE 5

(a) Preparation of
2-Hydroxy-3-[3-(1-piperidylmethyl)phenyl]-butyronitrile 0.74 g (3.2 mmol) of 2-[3-(1-piperidylmethyl)phenyl]-methyl-oxirane, 0.294 g (6 mmol) of sodium cyanide and 0.107 g (2 mmol) of ammonium chloride are boiled in 5 ml of ethanol/5 ml of water for 6 hours. After extensive concentration of the mother liquor by evaporation under vacuum, the residue is taken up with 10 ml of water, and the solution is adjusted to pH 12 with potassium carbonate and extracted with 3×20 ml of methylene chloride. After dehydration and concentration under vacuum, the organic phase yields 0.82 g of a brown oil.

(b) Preparation of
4-Amino-1-[3-(1-piperidylmethyl)phenyl]-2-butanol 0.10 g (2.6 mmol) of lithium aluminium hydride is added to 0.82 g (3.2 mmol) of 2-hydroxy-3-[3-(1-piperidylmethyl)phenyl]-butyronitrile in 30 ml of ether and 10 ml of tetrahydrofuran and the mixture is boiled under reflux for 2 hours. After the addition of 0.25 ml of water, the precipitate obtained is suction filtered, suspended in 20 ml of methylene chloride and again suction filtered. After dehydration of the combined organic phases and concentration by evaporation under vacuum, 0.65 g of a yellow oil is left behind, which is distilled in a high vacuum to yield 0.51 g (61%) of the title compound. Colourless, viscous oil, boiling point 140°–150° C./7×10$^{-3}$ mbar.

(c) Preparation of
3-[3-Hydroxy-4-[3-(1-piperidylmethyl)phenyl]butyl]amino-4-amino-1,2,5-thiadiazole-1-oxide

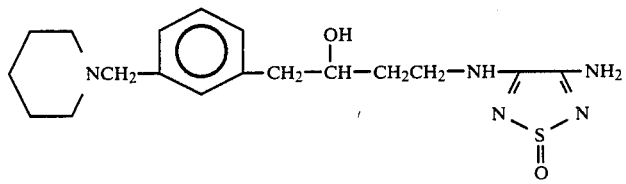

0.51 g (1.95 mmol) of 4-amino-1-[3-(1-piperidylmethyl)phenyl]-2-butanol in 5 ml of ethanol are added dropwise to 0.37 g (1.95 mmol) of 3,4-diethoxy-1,2,5-thiadiazole-1-oxide in 5 ml of ethanol by a method analogous to that of Example 1,c. After 4 hours at room temperature, 6 ml of ethanolic ammonia (5 mol/l) are added and the solution is stirred overnight. The solid obtained after evaporation of solvent under vacuum is chromatographed with methanol against silica gel.

Yield: 0.57 g (77%)
Colourless solid, melting point 74°–77° C.
Rf=0.47 (CH$_3$OH/NH$_3$ conc. 99:1)
C$_{18}$H$_{27}$N$_5$O$_5$ (377.5)
$^1$H-NMR spectrum: (d$_6$-DMSO, TMS as internal standard): δ=1.28–1.80 (m) 8H, 2.19–2.42 (m) 4H, 2.69 (d,broad) 2H, 3.23–3.92 (m) 4H, 3.38 (s) 2H, 4.70 (broad) 1H, replaceable by D$_2$O, 7.01–7.35 (m) 4H, 7.95 (broad) 2H, replaceable by D$_2$O

EXAMPLE 6

Preparation of
3-[2-Hydroxy-3-[3-(1-piperidylmethyl)benzyloxy]-propylamino]-4-amino-5-ethoxycarbonyl-isothiazole-1,1-dioxide

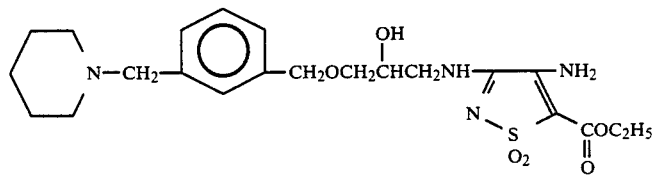

1.39 g (5 mmol) of 2-hydroxy-3-[3-(1-piperidylmethyl)benzyloxy]propylamine are added dropwise to a suspension of 1.24 g (5 mmol) of 4-amino-3-ethoxy-5-ethoxycarbonylisothiazole-1,1-dioxide in 10 ml of acetonitrile and the mixture is stirred for 5 hours at room temperature. The residue obtained after evaporation of the solvent under vacuum is chromatographed with methanol against silica gel. The main fraction yields 2.06 g (86%) of the title compound.

Colourless, amorphous solid, melting point 72°–74° C.

$Rf = 0.45$ ($CH_3OH/NH_3$ conc. 99:1)

$C_{22}H_{32}N_4O_6S$ (480.6)

$^1H$-NMR spectrum: ($d_6$-DMSO, TMS as internal standard): $\delta = 1.25$ (t) 3H, 1.30–1.66 (m) 6H, 2.21–2.47 (m) 4H, 3.20–3.77 (m) 4H, 3.44 (s) 2H, 3.93 (m) 1H, 4.23 (q) 2H, 4.51 (s) 2H, 7.28 (s) 4H, ~8.2 (broad) 3H, replaceable by $D_2O$

EXAMPLE 7

Preparation of
$N^1$-Cyano-$N^2$-methyl-$N^3$-[2-hydroxy-3-[3-(1-piperidylmethyl)benzyloxy]propyl]-guanidine

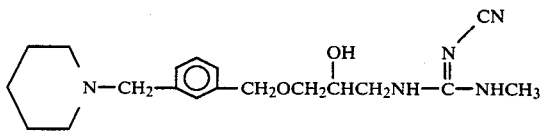

2.0 g (65 mmol) of methylamine are introduced at 0° to 3° C. with ice cooling into a solution of 1.9 g (5 mmol) of $N^1$-cyano-$N^2$-[2-hydroxy-3-[3-(1-piperidylmethyl)benzyloxy]propyl]-S-methyl-isothiourea in 30 ml of ethanol. After 2 hours' stirring at room temperature, the solvent is evaporated off under vacuum and the oil obtained is chromatographed with methylene chloride/methanol 1:1 against silica gel. After concentration by evaporation, the main fraction yields 1.2 g (67%) of the title compound in the form of a viscous, colourless oil.

$Rf = 0.72$ ($CH_3OH/NH_3$ conc. 99:1)

$C_{19}H_{29}N_5O_2$ (359.5)

$^1H$-NMR spectrum (CDCl$_3$, TMS as internal standard): $\delta = 1.23$–1.73 (m) 6H, 2.21–2.50 (m) 4H 2.71 (d) 3H, 3.17–3.61 (m) 4H, 3.48 (s) 2H, 3.92 (m) 1H, 4.49 (s) 2H, 4.60 (broad) 1H, replaceable by $D_2O$, 6.19 (t) 1H, replaceable by $D_2O$, 6.50 (q) 1H, replaceable by $D_2O$, 7.27 (s, broad) 4H

EXAMPLE 8

(a) Preparation
2-[2-Hydroxy-3-[5-(1-piperidylmethyl)-2-thienylthio]-propyl]-1H-isoindole-1,3-dione A mixture of 6.84 g (20 mmol) of 5-(1-piperidylmethyl)-2-S-isothiourea-methylthiophene-dihydrochloride and 6.1 g (30 mmol) of N-(2,3-epoxypropyl)-phthalimide is introduced into 50 ml of ethanol, and a solution of 2.4 g (60 mmol) of NaOH in 60 ml of ethanol is slowly added at 0° to 5° C. The mixture is then left to react for one hour at 0° to 5° C. and 3 hours at room temperature. The reaction solution is concentrated by evaporation under vacuum, the residue is taken up with $CH_2Cl_2/MeOH$ (80:20) and the organic phase is washed with water until neutral, dehydrated over $Na_2SO_4$ and concentrated by evaporation under vacuum. 8.3 g (96%) of the title compound are obtained as a brown oil.

(b) Preparation of
2-Hydroxy-3-[5-(1-piperidylmethyl)-2-thienylthio]-propylamine 8.60 g (20 mmol) of 2-[2-hydroxy-3-[5-(1-piperidylmethyl)-2-thienylthio]propyl]-1H-isoindole-1,3-dione and 3.3 ml of hydrazine hydrate (80%) are boiled in 80 of ethanol for 3 hours. The residue obtained after the mixture has been concentrated by evaporation is taken up in 50 ml of water. 8 ml of conc. hydrochloric acid are added and the mixture is filtered. The filtrate is adjusted to pH 12 with conc. sodium hydroxide solution and extracted with 3×40 ml methylene chloride. The organic phase is dehydrated with $Na_2SO_4$ and concentrated by evaporation under vacuum. 4.9 g (82% of theoretical) of the title compound are obtained in the form of a light green oil.

(c) Preparation of
3-[2-Hydroxy-3-[5-(1-piperidylmethyl)-2-thienylthio]-propylamino]-4-amino-1,2,5-thiadiazole-1-oxide

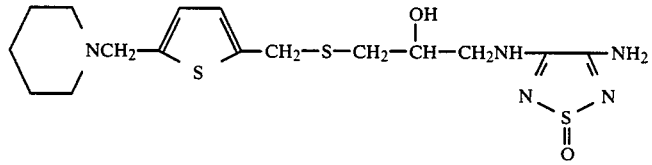

The compound is prepared by a method analogous to that of Example 1 c,d from 1.5 g (5 mmol) of 2-hydroxy-3-[5-(1-piperidylmethyl)-2-thienylthio]propylamine in 10 ml of ethanol and 0.95 g (5 mmol) of 3,4-diethoxy-1,2,5-thiadiazole-1-oxide.

Colourless crystals, melting point 171° C.

Yield: 1 g (48% of theoretical)

$Rf = 0.25$ ($CH_3OH$)

$C_{16}H_{25}N_5O_2S_3$ (415)

$^1H$-NMR spectrum: ($d_6$-DMSO, TMS as internal standard): $\delta = 1.20$–1.57 (m) 6H, 2.13–2.43 (m) 4H, 2.53 (d) 2H, 3.13–3.50 (m) 2H, 3.53 (s) 2H, 3.70–4.07 (m) 3H, 5.23 (s) 1H, replaceable by $D_2O$, 6.57–6.87 (m) 2H, 7.70–8.23 (m) 3H, replaceable by $D_2O$

EXAMPLE 9

(a) Preparation of
2-[2-Hydroxy-3-[5-(dimethylaminomethyl)-2-furfurylthio]propyl]-1H-isoindole-1,3-dione The compound is prepared by a method analogous to that of Example 8 a from 5-(dimethylaminomethyl)-2-S-isothiourea-methylfuran-bis-maleate and N-(2,3-epoxypropyl)phthalimide.

(b) Preparation of
2-Hydroxy-3-[5-(dimethylaminomethyl)-2-furfurylthio]propylamine The method of preparation is analogous to that of Example 8 b.

(c) Preparation of 3-[2-Hydroxy-3-[5-(dimethylaminomethyl)-2-furfurylthio]propylamino]-4-amino-1,2,5-thiadiaziole-1-oxide

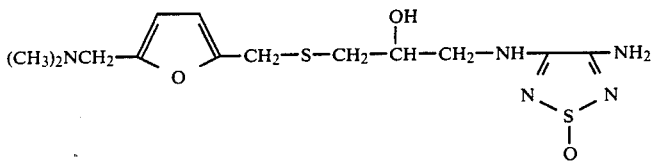

The method of preparation is analogous to that of Example 8 c.

Colourless crystals, melting point 131° C.

Rf=0.3 (CH₃OH)

$C_{13}H_{21}N_5O_3S_2$ (359): Calculated: C 43.45; H 5.85; N 19.50; Found: C 43.34; H 5.77; N 19.08

$^1H$-NMR spectrum: (d₆-DMSO, TMS as internal standard): δ=2.13 (s) 6H, 2.57 (d) 2H, 3.17–3.50 (m) 2H, 3.77 (m) 3H, 5.27 (broad) 1H, replaceable by D₂O, 6.17 (s) 2H, 7.80–8.27 (m) 3H, replaceable by D₂O

EXAMPLE 10

(a) Preparation of 2-[2-Hydroxy-3-[2-(guanidinothiazol-4-yl)methylthio]-propyl]-1H-isoindole-1,3-dione The compound is prepared by a method analogous to that of Example 8 a from [2-(guanidinothiazol-4-yl)methyl]-S-isothiourea-dihydrochloride and N-(2,3-epoxypropyl)-phthalimide.

(b) Preparation of 2-Hydroxy-3-[2-(guanidinothiazol-4-yl)methylthio]-propylamine The method of preparation is analogous to that of Example 8 b.

(c) Preparation of 3-[2-Hydroxy-3-[2-(guanidinothiazol-4-yl)methylthio]-propylamine]-4-amino-1,2,5-thiadiazole-1-oxide

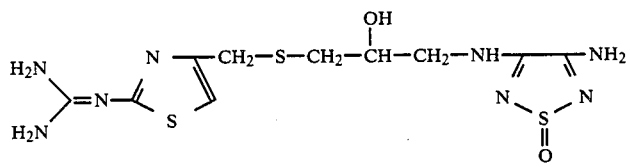

The method of preparation is analogous to that of Example 8c.

Colourless crystals, melting point 134°–135° C.

Rf=0.8 (CH₂Cl₂/CH₃OH 80:20)

$C_{10}H_{16}N_8O_2S_3$ (376)

$^1H$-NMR spectrum: (d₆-DMSO, TMS as internal standard): δ=2.60 (d) 2H, 3.23–4.17 (m) 5H, 5.27 (broad) 1H, replaceable by D₂O, 6.50 (s) 1H, 6.87 1 (broad) 4H, replaceable by D₂O, 7.80–8.40 (m) 3H, replaceable by D₂O

We claim:

1. A compound of the formula I

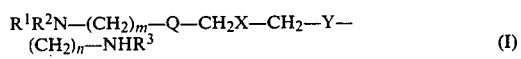

wherein R¹ and R², which may be identical or different, represent hydrogen, C₁₋₁₀-alkyl, C₅₋₆-cycloalkyl, amino, lower alkylamino or lower dialkylamino when m=1 or (NH₂)₂C= when m=0 or R¹ and R² together with the nitrogen atom to which they are attached represent a 5- to 8-membered heterocyclic ring which is unsubstituted or substituted with a methyl group, m stands for 0 or 1 and Q denotes a furan, thiophene, thiazole or benzene ring, X stands for a sulphur or oxygen atom or for the group —CHOH, Y represents a single bond or the group —CHOH, n denotes 1 or 2 and R³ represents one of the groups

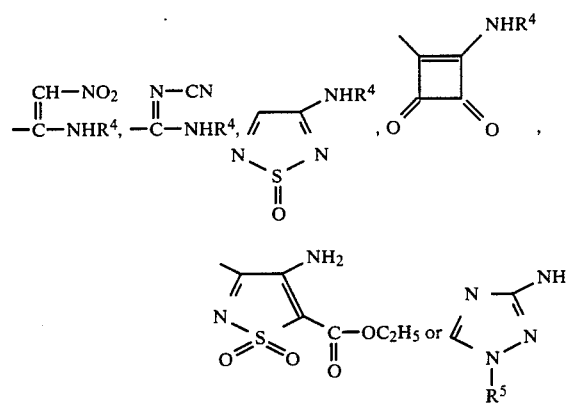

wherein R⁴ denotes a hydrogen atom, a C₁₋₃-alkyl group or a propargyl group and R⁵ denotes a hydrogen atom or a C₁₋₃-alkyl group, and their physiologically acceptable salts and hydrates.

2. A compound according to claim 1, characterised in that m=0, R¹ and R² each represents (NH₂)₂C=, Q represents a thiazole ring inserted in the 2,4-position, X represents a sulphur atom and Y represents the group —CHOH, n=1 and R³ has the meaning indicated in claim 1.

3. A compound according to claim 1, characterised in that m=1, R¹ and R², which may be identical or different, each represent C₁₋₃-alkyl or C₅₋₆-cycloalkyl or R¹ and R² together with the nitrogen atom to which they are attached represent a pyrrolidine, methylpyrrolidine, morpholine, thiomorpholine, piperidine, methylpiperidine, N-methylpiperazine, homopiperidine, heptamethyleneimino or octamethyleneimino ring, Q represents a thiophene ring inserted in the 2,5- or 2,4-position or a furan ring inserted in the 2,5-position, X denotes a sulphur atom, Y denotes the group —CHOH, n=1 and R³ has the meaning indicated in claim 1.

4. A compound according to claim 1, characterised in that m=1, $R^1$ and $R^2$, which may be identical or different, each represent $C_{1-3}$-alkyl or $C_{5-6}$-cycloalkyl or $R^1$ and $R^2$ together with the nitrogen atom to which they are attached represent a pyrrolidine, methylpyrrolidine, morpholine, thiomorpholine, piperidine, methylpiperidine, N-methylpiperazine, homopiperidine, heptamethyleneimino or octamethyleneimino ring, Q represents a benzene ring inserted in the remainder of the molecule by bonds in the 1- and 3- or in the 1- and 4-position, X denotes an oxygen atom, Y denotes the group —CHOH, n=1 and $R^3$ has the meaning indicated in claim 1.

5. A compound according to claim 1, characterised in that m=1, $R^1$ and $R^2$, which may be identical or different, each represents $C_{1-3}$-alkyl or $C_{5-6}$-cycloalkyl or $R^1$ and $R^2$ together with the nitrogen atom to which they are attached represent a pyrrolidine, methylpyrrolidine, morpholine, thiomorpholine, piperidine, methylpiperidine, N-methylpiperazine, homopiperidine, heptamethyleneimino or octamethyleneimino ring, Q represents a benzene ring inserted in the remainder of the molecular by bonds in the 1- and 3-position or 1- and 4-position, X denotes the group —CHOH, Y represents a single bond, n=1 and $R^3$ has the meaning indicated in claim 1.

6. A compound according to claim 1, characterised in that m=1, $R^1$ and $R^2$, which may be identical or different, each represent $C_{1-2}$-alkyl or $C_{5-6}$-cycloalkyl or $R^1$ and $R^2$ together with the nitrogen atom to which they are attached represent a pyrrolidine, methylpyrrolidine, morpholine, thiomorpholine, piperidine, methylpiperidine, N-methylpiperazine, homopiperidine, heptamethyleneimino or octamethyleneimino ring, Q represents a benzene ring inserted in the remainder of the molecule by bonds in the 1- and 3- or 1- and 4-position, X denotes the group —CHOH, Y represents a single bond, n=2 and $R^3$ has the meaning indicated in claim 1.

7. 3-[2-Hydroxy-3-[3-(1-piperidylmethyl)-benzyloxy]propylamino]-4-amino-1,2,5-thiadiazole-1-oxide and the physiologically acceptable salts and hydrates thereof.

8. 1-[2-Hydroxy-3-[3-(1-piperidylmethyl)benzyloxy]-propylamino]-2-amino-cyclobutene-3,4-dione and the physiologically acceptable salts and hydrates thereof.

9. 3-[2-Hydroxy-3-[3-(1-piperidylmethyl)benzyloxy]-propylamino]-4-amino-5-ethoxycarbonyl-isothiazole-1,1-dioxide and the physiologically acceptable salts and hydrates thereof.

10. A pharmaceutical composition for use in inhibiting the secretion of gastric acid and for the treatment of peptic ulcers and hyperacidic gastritis comprising as the principal active ingredient an effective amount of a compound according to claim 1 in admixture with a pharmaceutically acceptable carrier.

* * * * *